United States Patent [19]
Feelisch et al.

[11] Patent Number: 5,661,129
[45] Date of Patent: Aug. 26, 1997

[54] ORGANIC NITRATES CONTAINING A DISULFIDE GROUP AS CARDIOVASCULAR AGENTS

[75] Inventors: Martin Feelisch, Erkrath; Hilmar Bokens, Dusseldorf; Jochen Lehmann, Bonn; Claus Meese, Monheim; Klaus Sandrock, Langenfeld, all of Germany

[73] Assignee: Schwarz Pharma AG, Germany

[21] Appl. No.: 557,106

[22] PCT Filed: Jun. 24, 1994

[86] PCT No.: PCT/DE94/00726

§ 371 Date: Dec. 5, 1995

§ 102(e) Date: Dec. 5, 1995

[87] PCT Pub. No.: WO95/00477

PCT Pub. Date: Jan. 5, 1995

[30] Foreign Application Priority Data

Jun. 26, 1993 [DE] Germany .................. 43 21 306.5

[51] Int. Cl.$^6$ .................. A61K 38/05; A61K 38/06; C07K 5/00
[52] U.S. Cl. .................. 514/19; 514/18; 530/331; 558/482; 558/483; 930/260
[58] Field of Search ............ 514/18, 19; 530/331; 558/482, 483; 930/260

[56] References Cited

U.S. PATENT DOCUMENTS

| | | | |
|---|---|---|---|
| 5,284,872 | 2/1994 | Sandrock et al. | 514/509 |
| 5,428,061 | 6/1995 | Sandrock et al. | 514/509 |

*Primary Examiner*—Cecilia J. Tsang
*Assistant Examiner*—Bennett Celsa
*Attorney, Agent, or Firm*—Merchant, Gould, Smith, Edell, Welter & Schmidt, P.A.

[57] ABSTRACT

The invention relates to novel nitrates containing a disulphide group, and to processes for their preparation. The compounds can be used for the therapy of disorders of the cardiovascular system.

13 Claims, No Drawings

ORGANIC NITRATES CONTAINING A DISULFIDE GROUP AS CARDIOVASCULAR AGENTS

CROSS REFERENCE TO RELATED APPLICATION

This is a national application based on a PCT/DE94/00726 filed 24 Jun. 1994.

FIELD OF THE INVENTION

The invention relates to novel nitrates containing a disulphide group, and to processes for their preparation.

BACKGROUND OF THE INVENTION

Organic nitrates (esters of nitric acid) are proven medicinal substances for the treatment of heart diseases. They display their effect both by relieving the heart via a reduction in the preload and afterload and by improving the oxygen supply to the heart via coronary dilatation.

However, it has been found that the classical organic nitrates used in therapy, such as glycerol trinitrate, isosorbide dinitrate or isosorbide 5-mononitrate, display, on continuous intake of high doses, within a short time a distinct attenuation of the effect, nitrate tolerance. It has been possible to eliminate this deficiency using the compounds made available by EP 0 362 575 and EP 0 451 760.

According to EP 0 362 575 and EP 0 451 760, the effect of the nitro compounds is mediated by NO free radicals formed therefrom. Reaction of the nitrates with the thiol group of cysteine initially results in the formation of a reactive and short-lived intermediate product which is still hypothetical and is presumably the thiol ester of nitric acid or a thionitrate, which undergoes intramolecular rearrangement and subsequently decomposes to a pharmacologically active NO free radical and an unstable thio free radical which reacts with other thio free radicals to give the corresponding disulphide. The formation and release of the NO free radical requires a reduced thiol group-containing cysteine, which is converted into disulphides, so that the decrease in the effect of nitro compounds on continuing intake or administration of high doses is attributed to an exhaustion of the SH group pool. EP 0 362 575 and EP 0 451 760 claim compounds which contain sulphydryl groups and, on the basis of this general structural principle, prevent nitrate tolerance or diminish a nitrate tolerance which has already occurred.

SUMMARY OF THE INVENTION

It has now been found, surprisingly, that nitro compounds which, in place of a free thiol group, contain a disulphide group, are also effective and likewise display no nitrate tolerance on continuing intake. The present invention therefore relates to compounds of the general formula I

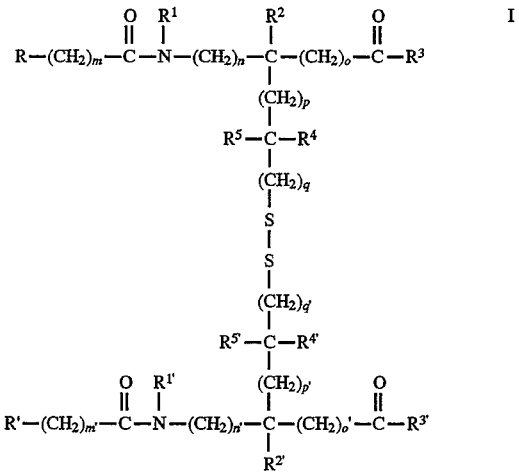

in which R and R' denote groups of the general formulae

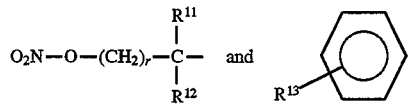

in which $R^{11}$ denotes hydrogen, alkyl having 1 to 6 carbon atoms, substituted lower alkyl in which the substituent is halogen, hydroxyl, lower alkoxy, aryloxy, amino, lower alkylamino, acylamino, acyloxy, arylamino, mercapto, lower alkylthio, arylthio, $R^{12}$ denotes like $R^{11}$ hydrogen or lower alkyl, $R^{13}$ is nitratoalkyl having 1 to 6 carbon atoms, r has the numerical values 0 to 10, and in which $R^1, R^{1'}$ denote hydrogen or lower alkyl, $R^2, R^{2'}$ is hydrogen, lower alkyl, phenyl, methoxyphenyl, phenyl-lower-alkyl, methoxyphenyl-lower-alkyl, hydroxyphenyl-lower-alkyl, hydroxy-lower-alkyl, alkoxy-lower-alkyl, amino-lower-alkyl, acylamino-lower-alkyl, mercapto-lower-alkyl or lower alkylthio-lower-alkyl, $R^3, R^{3'}$ are hydroxyl, lower alkoxy, lower alkenoxy, di-lower-alkylamino-lower-alkoxy, acylamino-lower-alkoxy, acyloxy-lower-alkoxy, aryloxy, aryl-lower-alkoxy, substituted aryloxy or substituted aryl-lower-alkoxy, in which the substituent is methyl, halogen or methoxy; amino, lower alkylamino, di-lower-alkylamino, aryl-lower-alkylamino, hydroxy-lower-alkyl-amino, pyrrolidine, piperidine, morpholine, piperazine or amino-acid residues via peptide linkage, $R^4, R^{4'}$ is hydrogen or lower alkyl, $R^5, R^{5'}$ denote like $R^4$, $R^{4'}$ hydrogen or lower alkyl, $R^2$ and $R^3$, and $R^{2'}$ and $R^{3'}$, can be linked together to form an ester or amide, $R^1$ and $R^2$, and $R^{1'}$ and $R^{2'}$, can be linked together to form an alkylene bridge having 2 to 4 carbon atoms, an alkylene bridge having 2 to 3 carbon atoms and a sulphur atom, an alkylene bridge having 3 to 4 carbon atoms, which contains a double bond or an alkylene bridge as above, substituted by hydroxyl, lower alkoxy, lower alkyl or di-lower-alkyl, m, n, o, p, q and m', n', o', p' and q' have the numerical values 0 to 10, and the physiologically tolerated salts thereof.

The present invention furthermore relates to compounds which have the following names:
- N'-3-nitratopivaloyl-L-cysteinamide-glutathione mixed disulphide,
- N'-3-nitratopivaloyl-L-cysteine ethyl ester-glutathione mixed disulphide,
- N'-3-nitratopivaloyl-L-cysteine ethyl ester-N'-acetyl-L-cysteine mixed disulphide,
- N-(3-nitratopivaloyl)-L-cysteine ethyl ester-D,L-penicillamine mixed disulphide,
- 2-acetylamino-3-[2-(2,2-dimethyl-3-nitrooxy-propionylamino)-2-ethoxycarbonylethyldisulphanyl]-3-methylbutyric acid.

These are asymmetric disulphides which generally contain sulphur-containing amino acids, especially glutathione or penicillamine.

The compounds according to the invention may also be in the form of their physiologically tolerated acid addition salts.

According to a further development of the invention, the aliphatic part(s) of the nitratoalkylarylalkanoic acid and nitratoalkanoic acid constituents has (have) a chain length of 2–6 carbon atoms; they may be straight-chain, branched, racemic or optically isomeric.

The nitratoalkane- and nitratoalkylarylalkanecarboxylic acid derivatives of the general formula (I) according to the invention preferably contain disulphides of sulphur-containing amino acids, in particular cystine, homocystine or penicillamine disulphide.

According to another development of the invention, the amino-acid disulphides are in the stereochemical L or DL form.

According to a particularly advantageous further development of the invention, the claimed compounds have the following chemical formulae:
N,N'-di(3-nitratopivaloyl)-L-cystine
N,N'-di(3-nitratopivaloyl)-D,L-homocystine
N,N'-di(3-nitratopivaloyl)-L-cystine diethyl ester
N,N'-di(3-nitratopivaloyl)-D,L-homocystine diethyl ester
N,N'-di(3-nitratopivaloyl)-L-cystine di-tert.-butyl ester
N,N'-di(4-nitratomethylbenzoyl)-L-cystine dimethyl ester
N,N'-di(3-nitratomethylbenzoyl)-L-cystine dimethyl ester
N,N'-di(4-nitratomethylbenzoyl)-L-cystine-di(N,N'-butylamide)
N,N'-di(3-nitratomethylbenzoyl)-L-cystine-di(N,N'-butylamide)
N,N'-di(4-nitratomethylbenzoyl)-L-cystinediamide
N,N'-di(3-nitratomethylbenzoyl)-L-cystinediamide
N,N'-di(3-nitratopivaloyl)-L-penicillamine disulphidediamide
N,N'-di(3-nitratopivaloyl)-L-cystinediamide
N,N'-di(3-nitratopivaloyl)-L-cystine-di(N,N'-methylamide)
N,N'-di(3-nitratopivaloyl)-L-cystine-di(N,N'-butylamide)
N,N'-di(3-nitratopivaloyl)-L-cystine-di(N,N'-tert-butylamide)
N,N'-di(3-nitratopivaloyl)-L-cystine-dimorpholide
N,N'-di(3-nitratopivaloyl)-L-cystinediisopropyl ester According to EP 0 362 575, the compounds according to the invention, of the general formula I, can be prepared in a manner known per se by condensing the appropriate nitrato carboxylic acid or its reactive derivatives with the amino group of a free, esterified or amidated amino-acid disulphide.

Compounds of the general formula I in which $R^3$ and $R^{3'}$ form, together with the adjacent carbonyl group, an amide functionality have an effect which, compared with the nitrates hitherto disclosed, has a delayed onset and is long lasting. This results in a reduced activation of the physiological counter-regulation elicited by the vasodilatation and permits the administration interval to be extended. The attenuation of compensatory mechanisms is particularly advantageous because it suggests a reduction of the side effects which occur during nitrate therapy, such as reflex tachycardia.

Compounds of the general formula I in which $R^3$ and $R^{3'}$ denote a substituted or unsubstituted amino group are therefore particularly preferred.

Alternatively, the relevant nitratoalkyl- or nitratoalkylarylalkyl-carboxylic acids or their reactive derivatives can initially be condensed with the amino group of an amino acid containing a thiol group to give the corresponding amide, which is subsequently oxidized with the aid of an oxidizing agent such as potassium iodate with dimerization to give the corresponding disulphide of the general formula I.

The preparation of these compounds by these methods leads, however, to inhomogeneous product mixtures in which the desired compounds are present only in small yield and require a high level of purification.

These disadvantages can be avoided by initially condensing the appropriate nitrato carboxylic acids or their reactive derivatives with the amino groups of free amino acids which are linked by disulphide bridges, converting the resulting compounds into activated esters on their carboxyl functionalities and subsequently reacting the latter with ammonia, a primary or a secondary amine to give the desired compounds. The invention therefore also relates to a process for the preparation of compounds of the general formula II

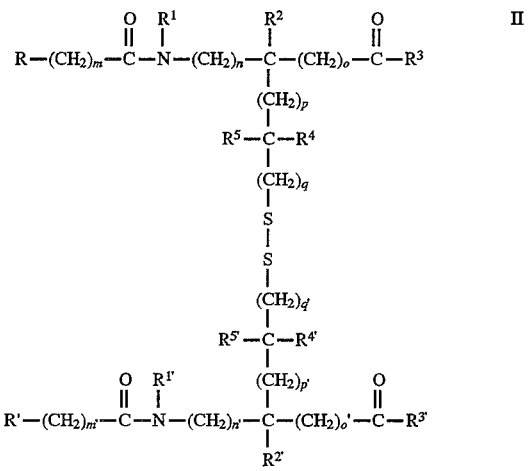

in which R and R' denote groups of the general formulae

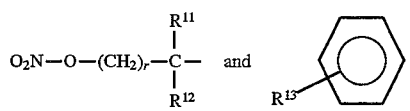

in which
$R^{11}$ denotes hydrogen, alkyl having 1 to 6 carbon atoms, substituted lower alkyl in which the substituent is halogen, hydroxyl, lower alkoxy, aryloxy, amino, lower alkylamino, acylamino, acyloxy, arylamino, mercapto, lower alkylthio, arylthio,
$R^{12}$ denotes like $R^{11}$ hydrogen or lower alkyl,
$R^{13}$ is nitratoalkyl having 1 to 6 carbon atoms,
r has the numerical values 0 to 10, and in which $R^1, R^{1'}$ denotes hydrogen or lower alkyl, $R^2, R^{2'}$ is hydrogen, lower alkyl, phenyl, methoxyphenyl, phenyl-lower-alkyl, methoxyphenyl-lower-alkyl, hydroxyphenyl-lower-alkyl, hydroxy-lower-alkyl, alkoxy-lower-alkyl, amino-lower-alkyl, acylamino-lower-alkyl, mercapto-lower-alkyl or lower alkylthio-lower-alkyl, $R^3, R^{3'}$ are amino, lower alkylamino, di-lower-alkylamino, aryl-lower-alkylamino, hydroxy-lower-alkylamino, pyrrolidine, piperidine, morpholine, piperazine or amino-acid residues via peptide linkage, $R^4, R^{4'}$ is hydrogen or lower alkyl, $R^5, R^{5'}$ denote like $R^4, R^{4'}$ hydrogen or lower alkyl, $R^1$ and $R^2$ and $R^{1'}$ and $R^{2'}$, can be linked together to form an alkylene bridge having 2 to 4 carbon atoms, an alkylene bridge having 2 to 3 carbon atoms and a sulphur atom, an alkylene bridge having 3 to 4 carbon atoms, which contains a double bond or an alkylene bridge as above, substituted by hydroxyl, lower alkoxy, lower alkyl or di-lower-alkyl, m, n, o, p, q and m', n', o', p' and q' have the numerical values 0 to 10, which is characterized in that compounds of the general formula III $$R-(CH_2)_m-\overset{O}{\overset{\|}{C}}-OH \qquad \text{III}$$

in which R denote groups of the general formulae

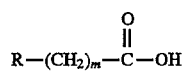 and 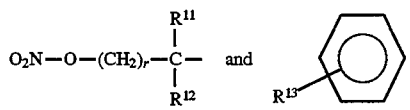

in which $R^{11}$ denotes hydrogen, alkyl having 1 to 6 carbon atoms, substituted lower alkyl in which the substituent is halogen, hydroxyl, lower alkoxy, aryloxy, amino, lower alkylamino, acylamino, acyloxy, arylamino, mercapto, lower alkylthio, arylthio, $R^{12}$ denotes like $R^{11}$ hydrogen or lower alkyl, $R^{13}$ is nitratoalkyl having 1 to 6 carbon atoms, m and r have the numerical value 0–10, in the form of their free acids, reactive halides, azides, esters and anhydrides are condensed in a manner known per se with compounds of the general formula IV

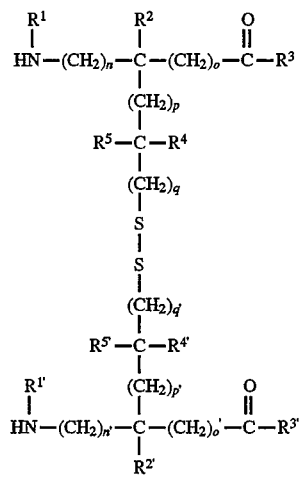

in which $R^1, R^{1'}$ denote hydrogen or lower alkyl, $R^2, R^{2'}$ is hydrogen, lower alkyl, phenyl, methoxyphenyl, phenyl-lower-alkyl, methoxyphenyl-lower-alkyl, hydroxyphenyl-lower-alkyl, hydroxy-lower-alkyl, alkoxy-lower-alkyl, amino-lower-alkyl, acylamino-lower-alkyl, mercapto-lower-alkyl or lower-alkylthio-lower-alkyl, $R^3, R^{3'}$ denotes hydroxyl or halogen, $R^4, R^{4'}$ is hydrogen or lower alkyl, $R^5, R^{5'}$ denote like $R^4, R^{4'}$ hydrogen or lower alkyl, $R^1$ and $R^2$, and $R^{1'}$ and $R^{2'}$, can be linked together to form an alkylene bridge having 2 to 4 carbon atoms, an alkylene bridge having 2 to 3 carbon atoms and a sulphur atom, an alkylene bridge having 3 to 4 carbon atoms, which contains a double bond or an alkylene bridge as above, substituted by hydroxyl, lower alkoxy, lower alkyl or di-lower-alkyl, n, o, p, q and n', o', p' and q' have the numerical values 0 to 10, to give compounds of the general formula V

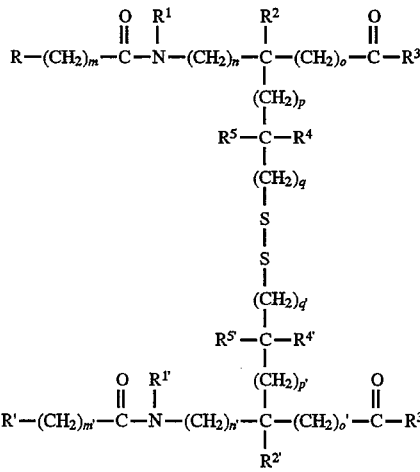

the latter are converted at their free or halogenated carboxyl functionalities with N-hydroxysuccinimide into activated carboxylic acid N-hydroxysuccinimide esters of the general formula VI

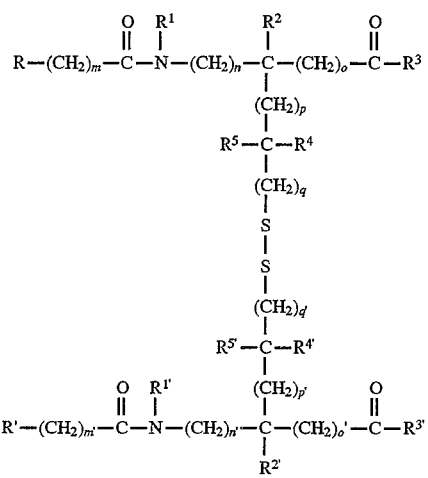

in which

R³ and R³' denotes, deviating from the above-mentioned meaning,

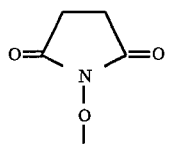

and the latter are subsequently reacted with ammonia, a primary or a secondary amine, in particular with lower alkylamine, di-lower-alkylamine, aryl-lower-alkylamine, hydroxy-lower-alkylamine, pyrrolidine, piperidine, morpholine, piperazine or amino acids to give the compounds of the general formula II.

DESCRIPTION OF PREFERRED EMBODIMENTS

The "lower alkyl radicals" mentioned in the general formulae are unbranched or branched hydrocarbon radicals having a maximum of 6 carbon atoms. Specific examples are the methyl, ethyl, propyl, isopropyl, butyl, isobutyl, tert.butyl, pentyl and isopentyl group. The lower alkoxy radicals likewise contain not more than 6 carbon atoms. Specific examples are the methoxy, ethoxy, propoxy, isopropoxy, butoxy, isobutoxy and tert.-butoxy groups. Preferred lower alkyl or alkoxy radicals contain not more than 4 carbon atoms. Radicals with 2 carbon atoms are particularly preferred. The preferred phenyl-substituted lower alkyl radical is the phenylmethyl group or the phenylethyl group.

The "lower alkanoyl radicals" are acyl radicals of fatty acids having 2–6 carbon atoms. Suitable halogen atoms are fluorine, chlorine, bromine and iodine atoms. Chlorine and bromine atoms are preferred.

"Aryl" denotes benzyl or phenyl radicals.

The substituted benzyl or phenyl radicals preferably have the substituent in position 4.

The hydroxy-substituted lower alkyl radicals have a hydroxyl group on an alkyl radical of the type described above, preferably on terminal carbon atoms. Specific examples are the hydroxymethyl and the 2-hydroxyethyl group.

The novel compounds of the general formula I and II according to the invention and their salts can be administered orally, enterally or parenterally in liquid or solid form.

The injection medium preferably used is water, which contains the additives customary for injection solutions, such as stabilizers, solubilizers or buffers. Examples of additives of these types are tartrate and citrate buffers, ethanol, complexing agents (such as ethylenediaminetetraacetic acid and its non-toxic salts), high molecular weight polymers (such as liquid polyethylene oxide) to regulate the viscosity. Examples of solid excipients are starch, lactose, mannitol, methylcellulose, talc, highly disperse silicas, high molecular weight fatty acids (such as stearic acid), gelatin, agar-agar, calcium phosphate, magnesium stearate, animal and vegetable fats and solid high molecular weight polymers (such as, for example, polyethylene glycols); formulations suitable for oral administration may, if desired, contain flavourings and sweeteners.

According to a further development of the invention, pharmaceuticals contain one and/or a mixture of the compounds according to the invention in admixture with pharmaceutically acceptable; i.e. conventional, excipients and ancillaries mentioned above.

These pharmaceuticals can be used for the treatment of disorders of the cardiovascular system, for example as compositions for the treatment of coronary heart disease, of high blood pressure and of heart failure and for dilatation of the peripheral vessels, including the cerebral and renal vessels.

Pharmaceutical formulations which contain a previously calculated amount of one or more of the compounds according to the invention can be administered once a day in the form of slow-release formulations or several times a day at regular intervals (2–3 times a day). The amounts of active substance which are normally administered each day are 20–300 mg per day, based on a bodyweight of 75 kg. The compounds according to the invention can be given in the form of injections 1–8 times a day or by continuous infusion. Amounts of 5–200 mg/day normally suffice.

A typical tablet may have the following composition:

| | |
|---|---|
| 1) N,N'-di(3-nitratopivaloyl)-L-cystinediamide | 30 mg |
| 2) Starch, U.S.P. | 57 mg |
| 3) Lactose, U.S.P. | 73 mg |
| 4) Talc, U.S.P. | 9 mg |
| 5) Stearic acid | 6 mg |

Substances 1, 2 and 3 are screened, granulated and mixed homogeneously with 4 and 5, and subsequently tabletted.

The exemplary embodiments illustrate the invention without being limited thereto.

EXAMPLE 1

Preparation of N,N'-di(3-nitratopivaloyl)-L-cystine 149.1 g (3.727 mol) of sodium hydroxide were dissolved in 2.5 l of water and cooled to 0° C. and, while stirring and cooling in an ice bath, 448.0 g (1.864 mol) of L-cystine were added in portions, during which 5° C. was not exceeded. To this were added 2.0 l of dichloromethane. Subsequently, while cooling and stirring vigorously, solutions consisting of 734.0 g (3.961 mol) of 3-nitratopivaloyl chloride in 1.0 l of dichloromethane and 167.8 g (4.195 mol) of sodium hydroxide in 1.0 l of water were slowly added dropwise simultaneously, during which the temperature rose to a maximum of 29° C. After stirring at room temperature for two and a half hours, the dichloromethane phase was separated off, the aqueous phase was washed with 0.1 l of dichloromethane and, while stirring, 350 ml of 37% strength (4.227 mol) of hydrochloric acid were added, whereupon an oily product precipitated. After extraction of this mixture three times with 2.0 l of ethyl acetate each time, the extracts were combined and concentrated in a ROTAVAPOR®, leaving a brown oily residue. This was dissolved in 2.0 l of boiling ethyl acetate and concentrated up to a constant weight under greatly reduced pressure (oil pump vacuum) at a bath temperature of about 55° C. (product foams greatly). The residue obtained in this way was dissolved in 1.0 l of boiling ethyl acetate, cooled to room temperature, diluted with 1.0 l of dichloromethane and induced to crystallize with the addition of seed crystals in a freezer at about −30° C. The crystallized substance was filtered off by suction, washed twice with 250 ml of a solution of 300 ml of dichloromethane and 200 ml of ethyl acetate at about −30° C. each time and dried to constant weight in a vacuum oven at about 40° C.

The yield was 318.03 g (corresponding to 32.16% of theory). Melting point 47.2° C.

EXAMPLE 2

Preparation of N,N'-di(3-nitratopivaloyl)-D,L-homocystine

Preparation and working up took place in analogy to Example 1. On acidification with 37% strength hydrochloric acid a solid product precipitated and was extracted with ethyl acetate and concentrated as described, leaving 51.3 g of white solid product (corresponding to 73.5% of theory).

This product was dissolved in 400 ml of methanol with heating, filtered and cooled to room temperature. To this were added, while stirring, 400 ml of distilled water, and the mixture was stirred at room temperature for 3 h, during which a product slowly crystallized out. This was filtered off with suction, washed once with a mixture consisting of 60 ml of distilled water and 40 ml of methanol and subsequently dried to a constant weight in a vacuum oven at about 40° C. under about 2 torr.

The yield was 31.3 g (corresponding to 44.8% of theory). Melting point about 42° C.

EXAMPLE 3

Preparation of N,N'-di(3-nitratopivaloyl)-L-cystine diethyl ester 24.4 g (82.9 mmol) of 3-nitratopivaloyl-L-cysteine ethyl ester were dissolved in 150 ml of glacial acetic acid at room temperature and, while stirring, a solution of 2.9 g (13.9 mmol) of potassium iodate in 300 ml of distilled water was slowly added dropwise, during which the mixture became brownish in colour and, after stirring for 15 min, a crystalline substance precipitated. The substance was filtered off with suction, dissolved in 150 ml of dichloromethane and washed successively once each with 100 ml of 1% strength sodium thiosulphate solution, 100 ml of 1N hydrochloric acid and 100 ml of distilled water. The dichloromethane phase was concentrated, the remaining residue (25.4 g) was dissolved in 150 ml of methanol, and 45 ml of distilled water were added. After addition of seed crystals, the substance crystallized at room temperature. To complete the crystallization, the flask was placed in a refrigerator (about 0° C.) overnight. The substance was filtered off with suction and washed twice with 30 ml of a mixture consisting of methanol and distilled water in the ratio 1:1, which was cooled to about −25° C., each time and dried to a constant weight in a vacuum oven over phosphorus pentoxide at about 35° C. under about 250 Pa.

The yield was 16.9 g (corresponding to 69.5% of theory). Melting point 84.9° C.

EXAMPLE 4

Preparation of di(nitratopivaloyl)-D,L-homocystine diethyl ester 11.4 g (35 mmol) of homocystine diethyl ester and 12.0 g (73.5 mmol) of 3-nitratopivalic acid were dissolved in 200 ml of dichloromethane, cooled to about 10° C. and, while stirring, a solution of 15.2 g (73.5 mmol) of DCC in 100 ml of dichloromethane was added dropwise in about 15 min, with DC-urea precipitating towards the end of the addition. The mixture was subsequently stirred at room temperature over the weekend, and the urea was filtered off with suction and washed twice with 50 ml of dichloromethane each time. The combined dichloromethane solutions were washed twice with 100 ml of 1N hydrochloric acid each time, twice with 100 ml of sodium bicarbonate solution each time and once with 100 ml of distilled water and concentrated in a ROTAVAPOR®, and the resulting residue was dissolved by heating in a mixture consisting of 175 ml of abs. ethanol and 25 ml of ethyl acetate. The resulting solution was filtered and placed in a refrigerator (0° C.) overnight. The crystals which formed during this were filtered off with suction and, after washing twice with 20 ml of abs. ethanol at about 0° C. each time, dried to constant weight in a vacuum oven at room temperature under about 250 Pa.

The yield was 12.4 g (corresponding to 57.6% of theory). Melting point 120.4° C.

EXAMPLE 5

Preparation of N,N'-di(3-nitratopivaloyl)-L-cystine di-tert.-butyl ester 17.76 g (0.03 mol) of L-cystine di-tert-butyl ester and 10.36 g (0.126 mol) of sodium acetate were dissolved in 80 ml of water and 120 ml of dichloromethane and, at 10° C. to 15° C., a solution of 12.0 g (0.066 mol) of 3-nitratopivaloyl chloride and 50 ml of dichloromethane was added dropwise. This mixture was stirred at room temperature overnight, and the organic phase was separated off and washed with 50 ml each of 1N hydrochloric acid and concentrated sodium bicarbonate solution. Drying over sodium sulphate was followed by filtration and concentration in a rotary evaporator.

The remaining residue was crystallized from ethanol, which was completed at −25° C. overnight, and was washed once with 10 ml of ethanol (−25° C.).

The yield was 12.73 g (corresponding to 66.02% of theory). Melting point 93.7° C.

EXAMPLE 6

Preparation of N,N'-di(4-nitratomethylbenzoyl)-L-cystine dimethyl ester 1.48 g (0.055 mol) of L-cystine dimethyl ester base were dissolved with stirring in 10 ml of methylene chloride, 0.56 g (0.055 mol) of triethylamine was added, and subsequently a solution of 2.16 g (0.01 mol) of 4-nitratomethylbenzoyl chloride in 10 ml of methylene chloride was slowly added dropwise. After stirring for 2 h, the product was filtered off with suction, washed with 2×15 ml of 1N hydrochloric acid and 2×15 ml of water, dried and recrystallized from ethyl acetate, resulting in colourless crystals.

The yield was 1.89 g (corresponding to 60.4% of theory). Melting point 155° C.

EXAMPLE 7

Preparation of N,N'-di(3-nitratomethylbenzoyl)-L-cystine dimethyl ester

The preparation took place in analogy to the 4-nitratomethylbenzoyl derivative. Since in this case the crude product remained in solution in the methylene chloride of the reaction mixture, after stirring for 2 h it was washed with 15 ml of 1N hydrochloric acid and 2×15 ml of water, dried, evaporated in vacuo and subsequently recrystallized from diisopropyl ether, resulting in colourless needles.

The yield was 2.68 g (corresponding to 85.6% of theory). Melting point 91° C.

EXAMPLE 8

Preparation of di-N,N'-(4-nitratomethylbenzoyl)-L-cystine-di-N,N'-butylamide 1.23 g (0.0035 mol) of L-cystine-di-N,N'-butylamide base were dissolved in 20 ml of methylene chloride, 0.61 g (0.006 mol) of triethylamine was added, and a solution of 1.29 g (0.006 mol) of 4-nitratomethylbenzoyl chloride in 10 ml of methylene chloride was slowly added dropwise. After stirring for 2 h, the mixture was washed with 20 ml of 1N hydrochloric acid and 2×15 ml of water, dried over sodium sulphate, evaporated to dryness in vacuo and recrystallized from methylene chloride, resulting in a colourless powder.

The yield was 0.93 g (corresponding to 26.3% of theory). Melting point 183° C.

EXAMPLE 9

Preparation of(S,S)-bis-N,N'-(3-nitratomethylbenzoyl)cystine-di-N,N'-butylamide

Took place in analogy to the 4-nitratomethylbenzoyl derivative.
Appearance: colourless powder
The yield was 0.4 g (corresponding to 11.3% of theory). Melting point 174°–175° C.

EXAMPLE 10

Preparation of N,N'-di(4-nitratomethylbenzoyl) cystinediamide 1.03 g (0.0035 mol) of cystinediamide base were suspended in 20 ml of methylene chloride, 0.60 g (0.006 mol) of triethylamine was added, and a solution of 1.29 g (0.006 mol of 4-nitratomethylbenzoyl chloride in 10 ml of methylene chloride was slowly added dropwise. After stirring overnight, the mixture was washed with 20 ml of 1N hydrochloric acid and 2×20 ml of water, dried over sodium sulphate and evaporated in a rotary evaporator, and the residue was recrystallized from methylene chloride, resulting in a colourless powder.

The yield was 0.32 g (corresponding to 15.3% of theory). Melting point 143° C.

EXAMPLE 11

Preparation of (S,S)-N,N'-bis(3-nitratomethylbenzoyl)cystinediamide took place in analogy to the 4-nitratomethylbenzoyl derivative, resulting in a colourless powder.

The yield was 0.25 g (corresponding to 12.2% of theory). Melting point 136° C.

EXAMPLE 12

Preparation of N,N'-di(3-nitratopivaloyl)-L-penicillamine disulphide-diamide

1st Stage: Preparation of L-penicillamine disulphide bisamide 7.95 g (0.02 mol) of L-penicillamine disulphide dimethyl ester×2 HCl were introduced into about 100 ml of liquid ammonia at −40° to −55° C. and stirred at −40° to −30° C. overnight, and the cooling bath was removed, whereupon the ammonia evaporated. The mixture was subsequently concentrated in a ROTAVAPOR® at a bath temperature of 50° C. and the entire residue was taken up in 40 ml of hot isopropanol and filtered. HCl gas was passed into the filtrate, whereupon the product was precipitated and was filtered off with suction.

The yield was 4.6 g (corresponding to 62.61% of theory).
2nd Stage: Preparation of N,N'-di(3-nitratopivaloyl)-L-penicillamine disulphide-diamide 4.41 g (12 mmol) of L-penicillamine disulphide bisamide×2 HCl and 4.03 g (48 mmol) of sodium bicarbonate were dissolved in 100 ml of water, 60 ml of dichloromethane were added, and the mixture was stirred until both phases were clear solutions. Then, at room temperature, a solution of 4.36 g (24 mmol) of 3-nitratopivaloyl chloride in 60 ml of dichloromethane was added dropwise, the mixture was stirred overnight, and the organic phase was separated off and washed twice with 50 ml of 1N hydrochloric acid each time. The dichloromethane was stripped off, leaving an oily residue which was purified by column chromatography.

The yield was 3.45 g (corresponding to 49.17% of theory).

EXAMPLE 13

Preparation of N,N'-di(3-nitratopivaloyl)-L-cystinediamide

1st Stage: preparation of N,N'-di(3-nitratopivaloyl)-L-cystine di(N-hydroxysuccinimide ester)

477.5 g (0.9 mol) of N,N'-di(3-nitratopivaloyl)-L-cystine (Example 1) and 213.4 g (1.854 mol) of N-hydroxysuccinimide were dissolved in 1400 ml of tetrahydrofuran, cooled to 5° C. and, while stirring and cooling in an ice bath, a solution of 382.5 g (1.854 mol) of DCC in 600 ml of tetrahydrofuran was added dropwise in 30 min. During this the temperature of the mixture rose to 30° C., and crystallization took place so that, to maintain stirring, initially 0.5 l of tetrahydrofuran was added and then it was heated to about 50° C. and subsequently further diluted with 0.5 l of acetone. The mixture was then stirred at about 50° C. for about 30 min, and the DC-urea was filtered off with suction (393.1 g dried=94.5% of theory) and washed with 0.5 l of acetone. The combined organic solutions were evaporated to dryness in a ROTAVAPOR®, the residue was dissolved by refluxing in 1.7 l of ethyl acetate, and the remaining residues of DC-urea (7.5 g=1.8% of theory) were filtered off. After standing at room temperature overnight, the substance which had crystallized out was separated off, washed twice with 0.2 l of ethyl acetate each time and dried to constant weight in a vacuum oven at room temperature under about 250 Pa.

The yield was 373.9 g (corresponding to 57.3% of theory)
2nd Stage: Preparation of N,N'-di(3-nitratopivaloyl)-L-cystinediamide 72.4 g (0.1 mol) of N,N'-di(3-nitratopivaloyl)-L-cystine di(N-hydroxysuccinimide ester) were dissolved in 300 ml of ethyl acetate. To this were added dropwise, while stirring, a solution consisting of 16.5 ml of (25% strength) ammonia solution and 60 ml of water, the mixture was stirred for 15 min, another solution consisting of 1.65 ml of (25% strength) ammonia solution and 6 ml of water was added, and the mixture was stirred for 30 min.

The organic phase was separated off, washed with 100 ml of water, dried with sodium sulphate and clarified with active charcoal, and the solvent was completely stripped off, leaving 56.72 g of residue. This was dissolved in 90 ml of methanol, 40 ml of water were added, and recrystallization took place at −25° C.

The precipitated product was filtered off with suction and washed twice with 25 ml of 1:1 methanol/water each time.

The yield was 37.4 g (corresponding to 70.75% of theory). Melting point 82.3° C.

EXAMPLE 14

Preparation of N,N'-di(3-nitratopivaloyl)-L-cystine-di(N-methylamide)

72.4 g (0.1 mol) of N,N'-di(3-nitratopivaloyl)-L-cystine di(N-hydroxysuccinimide ester) (Example 13, 1st stage) were dissolved in 300 ml of ethyl acetate and, while stirring at room temperature, a solution consisting of 19 ml of (40% strength) N-methylamine solution and 60 ml of water was added dropwise, and the mixture was stirred for 15 min. Then a further 1.7 ml were added and the mixture was stirred for 30 min.

The organic phase was separated off, washed with 100 ml of water, dried with sodium sulphate and clarified with active charcoal. The solvent was completely stripped off, leaving 59.44 g of residue. This was dissolved in 90 ml of methanol, 40 ml of water were added, and recrystallization took place.

The precipitated product was filtered off with suction and washed twice with 25 ml of 1:1 methanol/water each time.

The yield was 38.51 g (corresponding to 69.18% of theory). Melting point 166.5° C.

EXAMPLE 15

Preparation of N,N'-di(3-nitratopivaloyl)-L-cystine-di(N-butylamide)

7.3 g (0.01 mol) of N,N'-di(3-nitratopivaloyl)-L-cystine di(N-hydroxysuccinimide ester) (Example 13, 1st stage) were dissolved in 80 ml of dichloromethane at room temperature and, while stirring, a solution of 1.61 g (0.022 mol) of n-butylamine in 20 ml of dichloromethane was added, and the mixture was stirred for 1 hour. The organic phase was subsequently washed consecutively once each with 10 ml of 1N hydrochloric acid, 10 ml of 9% strength sodium bicarbonate solution and 10 ml of water and distilled in a ROTAVAPOR®, resulting in 5.7 g (=89.0% of theory) of residue which was recrystallized from 20 ml of methanol and 2 ml of H₂O at 0° C.

The yield was 4.3 g (corresponding to 67.1% of theory). Melting point 78.4° C.

EXAMPLE 16

Preparation of N,N'-di(3-nitratopivaloyl)-L-cystine-di(N-tert.-butylamide)

7.3 g (0.01 mol) of N,N'-di(3-nitratopivaloyl)-L-cystine di(N-hydroxysuccinimide ester) (Example 13, 1st stage) were dissolved in 80 ml of dichloromethane and, while stirring, a solution of 1.61 g (0.022 mol) of tert.-butylamine in 20 ml of dichloromethane was added, and the mixture was stirred for 1 hour. The organic phase was subsequently washed successively once each with 10 ml of 1N hydrochloric acid, 10 ml of 9% strength sodium bicarbonate solution and 10 ml of water and distilled in a ROTAVAPOR®, resulting in 6.19 (=95.2% of theory) of residue which was recrystallized from 25 ml of methanol and 2 ml of H₂O at 0° C.

The yield was 2.4 g (corresponding to 37.5% of theory). Melting point 81°–82° C.

EXAMPLE 17

Preparation of N,N'-di(3-nitratopivaloyl)-L-cystinedimorpholide 7.3 g (0.01 mol) of N,N'-di(3-nitratopivaloyl)-L-cystine di(N-hydroxysuccinimide ester) (Example 13, 1st stage) were dissolved in 80 ml of dichloromethane and, while stirring, a solution of 1.92 g (0.022 mol) of morpholine in 20 ml of dichloromethane was added dropwise, and the mixture was stirred at room temperature overnight. The organic phase was subsequently washed successively with 10 ml each of 1N hydrochloric acid, concentrated sodium bicarbonate solution and water, dried with sodium sulphate, filtered and completely removed by distillation, leaving 6.06 g (corresponding to 91.2% of theory) of residue which was purified by column chromatography.

The yield was 4.71 g (corresponding to 70.9% of theory). Melting point 33.6° C.

EXAMPLE 18

Preparation of N,N'-di(3-nitratopivaloyl)-L-cystine diisopropyl ester 7.3 g (10 mmol) of N,N'-di(3-nitratopivaloyl)-L-cystine di(N-hydroxysuccinimide ester) (Example 13, 1st stage) were dissolved in 150 ml of 2-propanol and stirred at room temperature overnight, and the 2-propanol was subsequently substantially stripped off in a ROTAVAPOR®. The remaining residue was taken up in 50 ml of dichloromethane, washed twice with 25 ml of water each time, dried over sodium sulphate and completely evaporated in a rotary evaporator, leaving a residue of 5.86 g of oil (95.28% of theory).

The latter was dissolved by heating in 35 ml of methanol and recrystallized at −25° C. The precipitated product was filtered off with suction, washed twice with 5 ml of methanol at low temperature each time and dried in a vacuum oven at room temperature.

The yield was 4.01 g (corresponding to 65.31% of theory). Melting point 88.2° C.

EXAMPLE 19

Preparation of N'-3-nitratopivaloyl-L-cysteinamide-glutathione mixed disulphide 3.1 g (10 mmol) of glutathione were dissolved in 10 ml of H₂O and mixed with a solution consisting of 5.3 g (10 mmol) of N,N'-di(3-nitratopivaloyl)-L-cystine-diamide (Example 13) in 50 ml of methanol under nitrogen gas, left to stand at room temperature for three days and subsequently evaporated to dryness in a ROTAVAPOR®. The 8.7 g of residue was dissolved in 30 ml of methanol and 20 ml of water and chromatographed on an RP-18 column using a Büchi chromatography system. The second fraction was evaporated to dryness in a ROTAVAPOR®, resulting in 1.5 g of residue which was dissolved by heating in 1 ml of water and 25 ml of ethanol. The substance which crystallized out in a refrigerator at 0° C. overnight was filtered off with suction, washed twice with 5 ml of ethanol at 0° C. each time and dried to constant weight over phosphorus pentoxide in a vacuum oven at room temperature under about 2 torr.

The yield was 0.87 g (corresponding to 15.3% of theory). Melting point 87.7° C.

EXAMPLE 20

Preparation of N-3-nitratopivaloyl-L-cysteine ethyl ester-glutathione mixed disulphide 17.7 g (60 mmol) of 3-nitratopivaloyl-L-cysteine ethyl ester were dissolved in 100 ml of acetic acid, and a solution consisting of 18.50 g (60 mmol) of glutathione in 85 ml of $H_2O$ and 50 ml of acetic acid was added. This mixture was stirred and cooled in a water bath (10° C.) while an aqueous solution consisting of 4.28 g (20 mmol) of potassium iodate in 65 ml of water was added dropwise over the course of about 30 mins until the mixture had a pale yellow colour (exothermic). After stirring at room temperature for a few min, a substance crystallized and was identified by thin-layer chromatography as N,N'-di(3-nitratopivaloyl)-L-cystine diethyl ester. 100 ml of water were added to the solution, which was cooled to about 0° C. and the crystallized substance was filtered off with suction, washed with 75 ml of water and dried (9.0 g=76.7% of theory). The mother liquor from this was evaporated to dryness in a ROTAVAPOR®, and the remaining residue was stirred with 100 ml of water and 250 ml of ethyl acetate. During this, a gelatinous product precipitated but could not be filtered off with suction and was therefore dissolved by adding 100 of 1N HCl. The combined aqueous solutions were evaporated to dryness in a ROTAVAPOR®, resulting in an oily residue (15.5 g). This was dissolved in 50 ml of water and adjusted to pH 4.5 with 25% strength ammonia solution. The adjusted solution was cooled to 0° C. but no crystallization took place. It was therefore again evaporated to dryness in a ROTAVAPOR® and chromatographed on an RP-18 column using a Büchi chromatography system. Since no fractionation took place, the solution was concentrated and the resulting residue (10.9 g) was fractionated using an Abimed chromatography system in 15 column runs. The combined second fractions were evaporated to dryness in a ROTAVAPOR®, and the remaining residue (1.2 g) was dissolved by heating in 25 ml of ethanol and 1.5 ml of water and placed in a refrigerator at 0° C. overnight. The product which crystallized out during this was filtered off with suction, washed twice with 5 ml of ethanol at 0° C. each time and dried to constant weight in a vacuum oven over phosphorus pentoxide at room temperature under about 2 torr.

The yield was 0.77 g (corresponding to 6.4% of theory). Melting point 167.6° C.

EXAMPLE 21

Preparation of N-3-nitratopivaloyl-L-cysteine ethyl ester-N-acetyl-L-cysteine mixed disulphide 5.9 g (20 mmol) of 3-nitratopivaloyl-L-cysteine ethyl ester were dissolved in 50 ml of acetic acid, and a solution consisting of 3.3 g (20 mmol) of N-acetyl-L-cysteine in 25 ml of water was added. This mixture was stirred and cooled in a water bath (10° C.) while an aqueous solution consisting of 1.43 g (0.66 mmol) of potassium iodate in 25 ml of water was added dropwise over the course of about 15 min until the mixture had a pale yellow colour (exothermic). After stirring at room temperature for a few min, a substance crystallized and was identified by thin-layer chromatography as N,N'-di(3-nitratopivaloyl)-L-cystine diethyl ester. 100 ml of water were added to the solution, which was cooled to about 0° C. and the substance which crystallized out filtered off with suction and dried (2.8 g=71.6% of theory). The mother liquor from this was evaporated to dryness in a ROTAVAPOR®. The remaining residue was stirred with 50 ml of water and 200 ml of ethyl acetate. The org. phase was separated off, washed successively once each with 50 ml of 1N HCl and 50 ml of $H_2O$, dried over sodium sulphate and evaporated to dryness in a Rotavapor®. 4.1 g of oily product remained after this and were purified by column chromatography on an RP column in a Büchi system. The residue from the second fraction evaporated in the ROTAVAPOR® (3.9 g) was dissolved in 10 ml of methanol, 15 ml of water were added, and the mixture was cooled to about 0° C. with stirring. The substance which crystallized out during this was filtered off with suction and dried to constant weight in a vacuum oven.

The yield was 2.4 g (corresponding to 79.0% of theory). Melting point Crystals, becoming viscous oil after a few weeks.

EXAMPLE 22

Preparation of N-(3-nitratopivaloyl)-L-cysteine ethyl ester-D,L-penicillamine mixed disulphide 8.82 g (30 mmol) of 3-nitratopivaloyl-L-cysteine ethyl ester were dissolved in 120 ml of methanol and, at 5° C.–10° C., a solution consisting of 4.50 g (30 mmol) of D,L-penicillamine in 40 ml of water and 20 ml of 1N hydrochloric acid was added. After addition of 2.14 g (10 mmol) of potassium iodate, the mixture was stirred at 10° C.–15° C. for about 1.5 h, then decolorized with sodium thiosulphate, and the crystallized residue was filtered off with suction at about 5° C. Drying in air resulted in 5.8 g of residue which was identified by thin-layer chromatography as N,N'-di(3-nitratopivaloyl)-L-cystine diethyl ester.

The filtrate was completely evaporated in a rotary evaporator, the residue was taken up in 100 ml of concentrated sodium acetate solution and clarified with 1 g of active charcoal at about 80° C., and 20 g of sodium chloride were added (clear solution). The product which crystallized in the refrigerator overnight was filtered off with suction and dried in a vacuum oven at room temperature.

The yield was 1.83 g (corresponding to 13.8% of theory). Melting point 132.5° C.

EXAMPLE 23

Preparation of 2-acetylamino-3-[2-(2,2-dimethyl-3-nitrooxypropionylamino)-2-ethoxycarbonylethyldisulphanyl]-3-methylbutyric acid 1.91 g (10 mmol) of N-acetyl-D,L-penicillamine and 2.94 g (10 mmol) of 3-nitratopivaloyl-L-cysteine ethyl ester were dissolved in 40 ml of methanol and 15 ml of water. At 15° C.–20° C., 710 mg (3.3 mmol) of potassium iodate were added in portions. (After addition of an additional spatula tip of potassium iodate, a permanent yellow coloration due to free iodine remained.) The mixture was decolorized by adding a little sodium thiosulphate and evaporated in a rotary evaporator. The residue was taken up in concentrated sodium bicarbonate solution ($CO_2$ evolution) and the N,N'-di(3-nitratopivaloyl)-L-cystine diethyl ester was removed by extraction several times with dichloromethane with TLC checks. The extracts were evaporated in a rotary evaporator, leaving a residue of 1.1 g.

The aqueous phase was acidified with concentrated hydrochloric acid and extracted with 50 ml of ethyl acetate. The ethyl acetate was completely stripped off, leaving a residue of 1.48 g.

The complete residue was purified by column chromatography in 150 mg portions (RP-18 column, Abimed chromatography system).

The residue from fraction 2 was recrystallized from 30 ml of 1/1 ethyl acetate/n-hexane.

The yield was 350 mg (corresponding to 7.24% of theory).

Melting point 120.2° C.

Pharmacological data

Vasorelaxation in vitro

The vasorelaxant effect of the compounds of the general formula I was investigated in vitro on isolated rat aortic rings. For this purpose, rats were anaesthetized and then the thoracic aorta was removed, freed of adipose and adventitious tissue and divided into annular segments about 5 mm wide. The aortic rings were transferred into temperature-controlled baths containing Tyrodes' solution through which 5% $CO_2$/95% $O_2$ was passed, and were subjected to a preload of 2 g. While continuously recording the change in force, the vascular rings were precontracted after equilibration with $2\times10^{-7}$ mol/l phenylephrine for 90 minutes. After a stable contraction level was reached, the nitrato compounds were cumulatively added to the vessel bath liquid, the next higher concentration in each case being added only after a stable relaxation level had been reached. The concentration of the particular compound which leads to a 50% relaxation of the precontracted vascular ring ($EC_{50}$) was found from the resulting concentration-effect plots. Table 1 contains the $EC_{50}$ values found in this way for selected exemplary compounds.

TABLE 1

| Substance | $EC_{50}$ [mol/l] | Number of individual tests [n] |
|---|---|---|
| N,N'-di(3-nitratopivaloyl)-L-cystine diethyl ester | $1.5 \times 10^{-6}$ | 6 |
| N,N'-di(3-nitratopivaloyl)-L-cystine | $1.2 \times 10^{-4}$ | 6 |
| N,N'-di(3-nitratopivaloyl)-L-cystinediamide | $3.0 \times 10^{-5}$ | 6 |
| N,N'-di(3-nitratopivaloyl)-L-cystinedi-tert.-butyl ester | $5.9 \times 10^{-5}$ | 3 |
| N,N'-di(3-nitratopivaloyl)-L-cystinedipiperidide | $1.0 \times 10^{-4}$ | 6 |
| N,N'-di(3-nitratopivaloyl)-L-cystinedi(N,N'-methylamide) | $2.4 \times 10^{-5}$ | 4 |

Effects on blood pressure in a conscious dog

To demonstrate the in vivo effect of the nitrates, the effects of the compounds according to the invention on the systolic arterial blood pressure (SAP), central venous blood pressure (CVP) and pulmonary artery blood pressure (PAP) were investigated in a conscious dog. The SAP was measured using a tip catheter transducer inserted into the aorta via the femoral artery, and the CVP and the PAP were measured using a Swan-Ganz catheter which was inserted via the left jugular vein and whose catheter tips were advanced as far as the pulmonary artery and the right atrium respectively and through whose lumens the particular pressure was passed to Statham® pressure transducers. To quantify the lowering of blood pressure elicited by the compound according to the invention, the areas under the curves (AUC) of the recorded changes in blood pressure were determined. Table 2 contains the AUC values for the relevant lowering of blood pressure after intravenous administration of 13.4 µg/kg of the disulphide compounds according to the invention and after intravenous administration of 26.8 µg/kg isosorbide 5-mononitrate (5-ISMN).

TABLE 2

|  | AUC (SAP) (mg) | AUC (CVP) (mg) | AUC (PAP) (mg) |
|---|---|---|---|
| N,N'-di(3-nitratopivaloyl)-L-cystine diethyl ester | 94.1 | 85.7 | 12.0 |
| N,N'-di(3-nitratopivaloyl)-L-cystine | 17.3 | 67.9 | 2.7 |
| N,N'-di(3-nitratopivaloyl)-L-cystinediamide | 55.3 | 46.9 | 28.1 |
| N,N'-di(3-nitratopivaloyl)-L-cystinedipiperidide | 10.4 | 36.9 | 18.5 |
| N,N'-di(3-nitratopivaloyl)-L-cystine-di(N,N'-methylamide) | 41.9 | 33.7 | 3.5 |
| 5-ISMN | 22.2 | 25.4 | 8.9 |

The distinctly larger AUC values compared with the classical nitrate 5-ISMN for the lowering of blood pressure after administration of the compounds according to the invention demonstrate their high activity.

We claim:

1. A compound of the formula

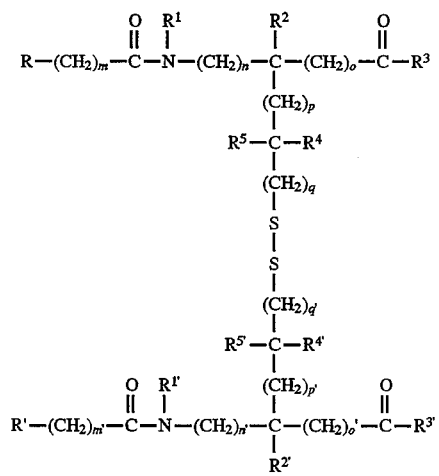

wherein R and R' are independently a group of the formulae $$O_2N-O-(CH_2)_r-\underset{R^{12}}{\overset{R^{11}}{\underset{|}{\overset{|}{C}}}}- \quad \text{or} \quad \underset{R^{13'}}{\bigcirc}$$

in which
- $R^{11}$ is hydrogen, $C_1$–$C_6$-alkyl, substituted $C_1$–$C_6$-alkyl in which the substituent is halogen, hydroxyl, $C_1$–$C_6$-alkoxy, aryloxy, amino, $C_1$–$C_6$-alkylamino, acylamino, acyloxy, arylamino, mercapto, $C_1$–$C_6$-alkylthio, arylthio,
- $R^{12}$ is hydrogen or $C_1$–$C_6$-alkyl,
- $R^{13}$ is nitratoalkyl having 1 to 6 carbon atoms, and
- r is an integer from 0 to 10;

and wherein
- $R^1$ and $R^{1'}$ are each independently hydrogen or $C_1$–$C_6$-alkyl;
- $R^2$ and $R^{2'}$ are each independently hydrogen, $C_1$–$C_6$-alkyl, phenyl, methoxy-phenyl, phenyl-$C_1$–$C_6$-alkyl, methoxyphenyl-$C_1$–$C_6$-alkyl, hydroxyphenyl-$C_1$–$C_6$-alkyl, hydroxy-$C_1$–$C_6$-alkyl, alkoxy-$C_1$–$C_6$-alkyl, amino-$C_1$–$C_6$-alkyl, acylamino-$C_1$–$C_6$-alkyl, mercapto-$C_1$–$C_6$-alkyl or $C_1$–$C_6$-alkylthio-$C_1$–$C_6$-alkyl,
- $R^3$ and $R^{3'}$ are each independently hydroxyl, $C_1$–$C_6$-alkoxy, $C_1$–$C_6$-alkenoxy, di-$C_1$–$C_6$-alkylamino-$C_1$–$C_6$-alkoxy, acylamino-$C_1$–$C_6$-alkoxy, acyloxy-$C_1$–$C_6$-alkoxy, aryloxy, aryl-$C_1$–$C_6$-alkoxy, substituted aryloxy or substituted aryl-$C_1$–$C_6$-alkoxy, in which the substituent is methyl, halogen or methoxy; amino, $C_1$–$C_6$-alkylamino, di-$C_1$–$C_6$-alkylamino, aryl-$C_1$–$C_6$-alkylamino, hydroxy-$C_1$–$C_6$-alkyl-amino, pyrrolidine, piperidine, morpholine, piperazine or amino-acid residues attached by a peptide bond;
- $R^4$ and $R^{4'}$ are each independently hydrogen or $C_1$–$C_6$-alkyl;
- $R^5$ and $R^{5'}$ are each independently hydrogen or $C_1$–$C_6$-alkyl;
- $R^2$ and $R^3$, and $R^{2'}$ and $R^{3'}$, can be linked together to form an ester or amide,
- $R^1$ and $R^2$, and $R^{1'}$ and $R^{2'}$, can be linked together to form an alkylene bridge having 2 to 4 carbon atoms, an alkylene bridge having 2 to 3 carbon atoms and a sulphur atom, an alkylene bridge having 3 to 4 carbon atoms, which contains a double bond or an alkylene bridge as above, substituted by hydroxyl, $C_1$–$C_6$-alkoxy, $C_1$–$C_6$-alkyl or di-$C_1$–$C_6$-alkyl,
- m, n, o, p, q and m', n', o', p' and q' are each independently integers from 0 to 10, or a physiologically tolerated acid addition salt thereof.

2. A compound according to claim 1, wherein the nitratoalkane- or nitratoalkylarylalkanecarboxylic acid groups have a chain length of 2 to 6 carbon atoms which are straight-chain, branched, racemic or an optical isomer thereof where the groups contain an asymmetric carbon atom.

3. A compound according to claim 1, wherein an amino-acid disulphide is a cystine, homocystine or penicillamine disulphide.

4. A compound according to claim 3, wherein the amino-acid disulphide is in the stereochemical L form.

5. A compound according to claim 3, wherein the amino-acid disulphide is in the stereochemical D,L form.

6. A compound selected from the group consisting of
N,N'-di(3-nitratopivaloyl)-L-cystine,
N,N'-di (3-nitratopivaloyl)-D,L-homocystine,
N,N'-di(3-nitratopivaloyl)-L-cystine diethyl ester,
N,N'-di(3-nitratopivaloyl)-D,L-homocystine diethyl ester,
N,N'-di(3-nitratopivaloyl)-L-cystine-di-(2-methyl-2-propylester),
N,N'-di(4-nitratomethylbenzoyl)-L-cystine dimethyl ester,
N,N'-di(3-nitratomethylbenzoyl)-L-cystine dimethyl ester,
N,N'-di(4-nitratomethylbenzoyl)-L-cystine di(N,N'-butyl-amide),
N,N'-di(3-nitratomethylbenzoyl)-L-cystine-di(N,N'-butyl-amide),
N,N'-di(4-nitratomethylbenzoyl)-L-cystinediamide,
N,N'-di(3-nitratomethylbenzoyl)-L-cystinediamide,
N,N'-di(3-nitratopivaloyl)-L-penicillamine-disulphide-diamide,
N,N'-di(3-nitratopivaloyl)-L-cystinediamide,
N,N'-di(3-nitratopivaloyl)-L-cystine-di(N,N'-methylamide),
N,N'-di(3-nitratopivaloyl)-L-cystine-di(N,N'-butylamide),
N,N'-di(3-nitratopivaloyl)-L-cystine-di(N,N'-tert.-butyl-amide),
N,N'-di(3-nitratopivaloyl)-L-cystine-dimorpholide, and
N,N'-di(3-nitratopivaloyl)-L-cystinediisopropyl ester, or a physiologically tolerated acid addition salt thereof.

7. A compound selected from the group consisting of
-N'-3-nitratopivaloyl-L-cysteinamide-glutathione mixed disulphide,
-N'-3-nitratopivaloyl-L-cysteine ethyl ester-glutathione mixed disulphide,
-N'-3-nitratopivaloyl-L-cysteine ethyl ester-N'acetyl-L-cysteine mixed disulphide,
-N-(3-nitratopivaloyl)-L-cysteine ethyl ester-D,L-penicillamine mixed disulphide, and
-2-acetylamino-{-3-2-(2 2-dimethyl-3-nitrooxy-propionyl-amino)-ethoxycarbonylethyldisulphanyl}-3-methylbutyric acid.

8. A pharmaceutical composition comprising a therapeutically effective amount of at least one compound according to claim 1 in admixture with pharmaceutically acceptable excipients.

9. A pharmaceutical composition comprising a therapeutically effective amount of at least one compound according to claim 6 in admixture with pharmaceutically acceptable excipients.

10. A pharmaceutical composition comprising a therapeutically effective amount of at least one compound according to claim 7 in admixture with pharmaceutically acceptable excipients.

11. A method for treating cardiovascular disorders comprising administering to a host in need thereof the pharmaceutical composition according to claim 8.

12. A method for treating cardiovascular disorders comprising administering to a host in need thereof the pharmaceutical composition according to claim 9.

13. A method for treating cardiovascular disorders comprising administering to a host in need thereof the pharmaceutical composition according to claim 10.

* * * * *

UNITED STATES PATENT AND TRADEMARK OFFICE
CERTIFICATE OF CORRECTION

PATENT NO. : 5,661,129

DATED : August 26, 1997

INVENTOR(S) : Martin Feelisch et al.

It is certified that error appears in the above-identified patent and that said Letters Patent is hereby corrected as shown below:

On column 20, line 39 (claim 7), please delete "-{-3-2-(2 2-" and substitute therefore -- -3-{2-(2,2- --

Signed and Sealed this

Twenty-eighth Day of April, 1998

*Attest:*

BRUCE LEHMAN

*Attesting Officer*    Commissioner of Patents and Trademarks